US012247084B2

(12) United States Patent
Friedman et al.

(10) Patent No.: US 12,247,084 B2
(45) Date of Patent: Mar. 11, 2025

(54) ANTI-BCMA CAR ANTIBODIES, CONJUGATES, AND METHODS OF USE

(71) Applicant: 2seventy bio, Inc., Cambridge, MA (US)

(72) Inventors: Kevin Friedman, Melrose, MA (US); Molly Reed Perkins, Milton, MA (US)

(73) Assignee: 2seventy bio, Inc., Cambridge, MA (US)

( * ) Notice: Subject to any disclaimer, the term of this patent is extended or adjusted under 35 U.S.C. 154(b) by 1126 days.

(21) Appl. No.: 16/973,877

(22) PCT Filed: Jun. 14, 2019

(86) PCT No.: PCT/US2019/037274
§ 371 (c)(1),
(2) Date: Dec. 10, 2020

(87) PCT Pub. No.: WO2019/241686
PCT Pub. Date: Dec. 19, 2019

(65) Prior Publication Data
US 2021/0261689 A1    Aug. 26, 2021

Related U.S. Application Data

(60) Provisional application No. 62/685,043, filed on Jun. 14, 2018.

(51) Int. Cl.
| | |
|---|---|
| *C07K 16/42* | (2006.01) |
| *A61K 39/00* | (2006.01) |
| *G01N 33/569* | (2006.01) |
| *G01N 33/58* | (2006.01) |
| G01N 33/533 | (2006.01) |
| G01N 33/563 | (2006.01) |
| G01N 33/68 | (2006.01) |

(52) U.S. Cl.
CPC ...... *C07K 16/4258* (2013.01); *C07K 16/4241* (2013.01); *G01N 33/56972* (2013.01); *G01N 33/583* (2013.01); *C07K 2317/21* (2013.01); *C07K 2317/24* (2013.01); *C07K 2317/34* (2013.01); *C07K 2317/622* (2013.01); *G01N 2333/70578* (2013.01)

(58) Field of Classification Search
None
See application file for complete search history.

(56) References Cited

U.S. PATENT DOCUMENTS

| | | |
|---|---|---|
| 4,671,958 A | 6/1987 | Rodwell et al. |
| 5,585,089 A | 12/1996 | Queen et al. |
| 5,665,357 A | 9/1997 | Rose et al. |
| 2016/0046724 A1* | 2/2016 | Brogdon ............ C07K 14/7051 435/328 |
| 2017/0051068 A1 | 2/2017 | Pillarisetti et al. |
| 2018/0162952 A1 | 6/2018 | Foord et al. |
| 2023/0030085 A1 | 2/2023 | Friedman et al. |

FOREIGN PATENT DOCUMENTS

| | | |
|---|---|---|
| EP | 0404097 A2 | 12/1990 |
| WO | WO 1993/001161 A1 | 1/1993 |
| WO | WO 93/06213 A1 | 4/1993 |
| WO | WO 2012/030982 A1 | 3/2012 |
| WO | WO 2014/190273 A1 | 11/2014 |
| WO | WO-2016/014565 A2 | 1/2016 |
| WO | WO 2016/014789 A2 | 1/2016 |
| WO | WO-2016/094304 A2 | 6/2016 |
| WO | WO 2017/031104 A1 | 2/2017 |
| WO | WO-2018/022786 A1 | 2/2018 |
| WO | WO-2018/156791 A1 | 8/2018 |
| WO | WO-2018/231759 A1 | 12/2018 |
| WO | WO-2019/161035 A1 | 8/2019 |

OTHER PUBLICATIONS

Bellucci, Roberto, et al. "Graft-versus-tumor response in patients with multiple myeloma is associated with antibody response to BCMA, a plasma-cell membrane receptor." Blood (2005); 105.10: 3945-3950.
Boerner et al., "Production of antigen-specific human monoclonal antibodies from in vitro-primed human splenocytes," J Immunol. Jul. 1, 1991;147(1):86-95.
Borden and Kabat, "Nucleotide sequence of the cDNAs encoding the variable region heavy and light chains of a myeloma protein specific for the terminal nonreducing end of alpha(1-6)dextran", Proc Natl Acad Sci U S A (1987);84(8):2440-2443.
Brodeur et al., Monoclonal Antibody Production Techniques and Applications, pp. 51-63 (Marcel Dekker, Inc., New York, 1987).
Bruggermann et al., "Designer mice: the production of human antibody repertoires in transgenic animals," Year Immunol. 1993;7:33-40.
Chothia and Lesk, "Canonical structures for the hypervariable regions of immunoglobulins", J Mol Biol (1987); 196(4):901-917.
Chothia, C. et al., "Conformations of immunoglobulin hypervariable regions", Nature (1989); 342(6252):877-883.
Holliger, Philipp, et al. "Diabodies: small bivalent and bispecific antibody fragments." Proceedings of the National Academy of Sciences (1993); 90.14: 6444-6448.
Holt, L. et al., "Domain antibodies: proteins for therapy", Trends in Biotechnology (2003); 21(11):484-490.
Hudson, Peter J., and Souriau, Christelle. "Engineered antibodies." Nature medicine 9.1 (2003): 129-134.
International Search Report and Written Opinion mailed on Oct. 1, 2019, for International Application No. PCT/US2019/037274, 8 pages.
Jakobovits et al., "Analysis of homozygous mutant chimeric mice: deletion of the immunoglobulin heavy-chain joining region blocks B-cell development and antibody production," Proc Natl Acad Sci U S A. Mar. 15, 1993;90(6):2551-5.
Jakobovits et al., "Germ-line transmission and expression of a human-derived yeast artificial chromosome," Nature, 362: 255 (1993).

(Continued)

*Primary Examiner* — Michael Szperka
*Assistant Examiner* — Marianne Dibrino
(74) *Attorney, Agent, or Firm* — Foley Hoag LLP; Ariana D. Harris; Samantha N. Devenport

(57) ABSTRACT

The invention provides improved methods for detecting anti-BCMA CAR expression on T cells.

14 Claims, 1 Drawing Sheet
Specification includes a Sequence Listing.

(56) References Cited

OTHER PUBLICATIONS

Kalled, "The role of BAFF in immune function and implications for autoimmunity," Immunological Reviews, 2005, vol. 204: 43-54.

Kozbor et al., "A human hybrid myeloma for production of human monoclonal antibodies," J Immunol. Dec. 1984;133(6):3001-5.

Laabi, Y., et al. "A new gene, BCM, on chromosome 16 is fused to the interleukin 2 gene by at (4; 16)(q26; p13) translocation in a malignant T cell lymphoma." The EMBO Journal (1992); 11.11: 3897-3904.

Laabi, Yacine, et al. "The BCMA gene, preferentially expressed during B lymphoid maturation, is bidirectionally transcribed." Nucleic Acids Research (1994); 22.7: 1147-1154.

MacKay et al., "BAFF and April: A Tutorial on B Cell Survival," Annu. Rev. Immunol., 2003, 21: 231-264.

Moreaux, Jérôme, et al. "BAFF and April protect myeloma cells from apoptosis induced by interleukin 6 deprivation and dexamethasone." Blood (2004); 103.8: 3148-3157.

Neri, Paola, et al. "Neutralizing B-Cell-Activating Factor Antibody Improves Survival and InhibitsOsteoclastogenesis in a Severe Combined Immunodeficient Human Multiple Myeloma Model." Clinical Cancer Research (2007); 13.19: 5903-5909.

Ng et al., "B Cell-Activating Factor Belonging to the TNF Family (BAFF)-R Is the Principal BAFF Receptor Facilitating BAFF Costimulation of Circulating T and B Cells." Journal of Immunology (2004); 173(2): 807-817.

Novak, Anne J., et al. "Expression of BCMA, TACI, and BAFF-R in multiple myeloma: a mechanism for growth and survival." Blood (2004); 103.2: 689-694.

O'Connor, Brian P., et al. "BCMA is essential for the survival of long-lived bone marrow plasma cells." Journal of Experimental Medicine (2004); 199.1: 91-97.

Orlandi, R. et al., "Cloning immunoglobulin variable domains for expression by the polymerase chain reaction", Proc Natl Acad Sci USA (1989); 86(10):3833-3737.

Plückthun, A. "Antibodies from *Escherichia coli*." The Pharmacology of Monoclonal Antibodies. (eds. Rosenburg and Moore), Springer Berlin Heidelberg (1994); 113: 269-315.

Schiemann, Barbara, et al. "An essential role for BAFF in the normal development of B cells through a BCMA-independent pathway." Science (2001); 293.5537: 2111-2114.

Thompson et al., "BAFF Binds to the Tumor Necrosis Factor Receptor-like Molecule B Cell Maturation Antigen and Is Important for Maintaining the Peripheral B Cell Population," J. Exp. Med., vol. 192, No. 1, Jul. 3, 2000, pp. 129-135.

Whitelegg N & Rees AR, "WAM: an improved algorithm for modelling antibodies on the Web," Protein Eng. Dec. 2000;13(12):819-24.

Whitelegg N & Rees AR, "Antibody variable regions: toward a unified modeling method," Methods Mol Biol. 2004;248:51-91.

Wu and Kabat, "An analysis of the sequences of the variable regions of Bence Jones proteins and myeloma light chains and their implications for antibody complementarity", J Exp Med. (1970); 132(2): 211-250.

Xu, Shengli, and Lam, Kong-Peng. "B-cell maturation protein, which binds the tumor necrosis factor family members BAFF and April, is dispensable for humoral immune responses." Molecular and Cellular Biology (2001); 21.12: 4067-4074.

Conde et al., "Revisiting 30 years of biofunctionalization and surface chemistry of inorganic nanoparticles for nanomedicine" Frontiers in Chemistry, Jul. 15, 2014, vol. 2, article 48, 27 pages.

Extended European Search Report for EP Application No. 19820088.3 dated Feb. 16, 2022, 9 pages.

Hu et al., "The Chimeric Antigen Receptor Detection Toolkit," Frontiers in Immunology, Aug. 11, 2020, vol. 11, pp. 1-16.

International Search Report and Written Opinion for International Application No. PCT/US2020/065352, dated Mar. 15, 2021, 10 pages.

Jena et al., "Chimeric Antigen Receptor (CAR)-Specific Monoclonal Antibody to Detect CD19-Specific T Cells in Clinical Trials", PLoS One, vol. 8, No. 3, Mar. 1, 2013 (Mar. 1, 2013), p. e57838.

Reichman et al., "Comparison of FACS and PCR for Detection of BCMA-CAR-T Cells," International Journal of Molecular Sciences, Jan. 14, 2022, vol. 23, No. 2, 14 pages.

Smith et al., "Development and Evaluation of an Optimal Human Single-Chain Variable Fragment-Derived BCMA-Targeted CART Cell Vector," Mol Ther. Jun. 6, 2018;26(6):1447-1456.

Supplementary European Search Report for European Application No. EP19820088.3, dated Mar. 9, 2022, 10 pages.

Extended European Search Report for EP Application No. 20902960.2 dated Mar. 7, 2024.

\* cited by examiner

SEQUENCE LISTING

<160> NUMBER OF SEQ ID NOS: 41

<210> SEQ ID NO 1
<211> LENGTH: 11
<212> TYPE: PRT
<213> ORGANISM: Artificial Sequence
<220> FEATURE:
<223> OTHER INFORMATION: Made in Lab - Light chain CDR1

<400> SEQUENCE: 1

Lys Ala Ser Gln Asp Val Asp Thr Thr Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Made in Lab - Light chain CDR2

<400> SEQUENCE: 2

Trp Ala Ser Thr Arg His Thr
1               5

<210> SEQ ID NO 3
<211> LENGTH: 9
<212> TYPE: PRT

<213> ORGANISM: Artificial Sequence
<220> FEATURE:
<223> OTHER INFORMATION: Made in Lab - Light Chain CDR3

<400> SEQUENCE: 3

Gln Gln Tyr Thr Phe Tyr Pro Tyr Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Made in Lab - Heavy chain CDR1

<400> SEQUENCE: 4

Gly Tyr Thr Phe Thr Ser Tyr Trp Met His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Made in Lab - Heavy chain CDR2

<400> SEQUENCE: 5

Glu Ile Asn Pro Arg Asn Gly Arg Ser Asn Tyr Asn Glu Lys Phe Lys
1               5                   10                  15

Thr

<210> SEQ ID NO 6
<211> LENGTH: 14
<212> TYPE: PRT
<213> ORGANISM: Artificial Sequence
<220> FEATURE:
<223> OTHER INFORMATION: Made in Lab - Heavy chain CDR6

<400> SEQUENCE: 6

Glu Val His Tyr Tyr Gly Ser Asp Tyr Asp Ala Met Asp Phe
1               5                   10

<210> SEQ ID NO 7
<211> LENGTH: 107
<212> TYPE: PRT
<213> ORGANISM: Artificial Sequence
<220> FEATURE:
<223> OTHER INFORMATION: Made in Lab - Varialble light chain

<400> SEQUENCE: 7

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asp Thr Thr
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Thr Phe Tyr Pro Tyr
                85                  90                  95

Thr Phe Gly Gly Gly Thr Lys Leu Glu Ile Lys

-continued

```
                100                 105

<210> SEQ ID NO 8
<211> LENGTH: 123
<212> TYPE: PRT
<213> ORGANISM: Artificial Sequence
<220> FEATURE:
<223> OTHER INFORMATION: Made in Lab - Variable heavy chain

<400> SEQUENCE: 8

Glu Val Gln Leu Gln Glu Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Arg Asn Gly Arg Ser Asn Tyr Asn Glu Lys Phe
    50                  55                  60

Lys Thr Lys Ala Thr Leu Thr Val Asp Glu Ser Ser Thr Ala Tyr
65                  70                  75                  80

Met Gln Leu Ser Ser Leu Thr Ser Glu Asp Ser Ala Val Tyr Ser Cys
            85                  90                  95

Ala Arg Glu Val His Tyr Tyr Gly Ser Asp Tyr Asp Ala Met Asp Phe
            100                 105                 110

Trp Gly Gln Gly Thr Ser Val Thr Val Ser Ser
        115                 120

<210> SEQ ID NO 9
<211> LENGTH: 11
<212> TYPE: PRT
<213> ORGANISM: Artificial Sequence
<220> FEATURE:
<223> OTHER INFORMATION: Made in Lab - Light chain CDR1

<400> SEQUENCE: 9

Lys Ala Ser Gln Asp Val Gly Thr Ala Val Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Made in Lab - Light chain CDR2

<400> SEQUENCE: 10

Trp Ala Ser Thr Arg His Thr
1               5

<210> SEQ ID NO 11
<211> LENGTH: 9
<212> TYPE: PRT
<213> ORGANISM: Artificial Sequence
<220> FEATURE:
<223> OTHER INFORMATION: Made in Lab - Light Chain CDR3

<400> SEQUENCE: 11

Gln Gln Tyr Asn Thr Tyr Pro Tyr Thr
1               5

<210> SEQ ID NO 12
<211> LENGTH: 10
<212> TYPE: PRT
```

```
<213> ORGANISM: Artificial Sequence
<220> FEATURE:
<223> OTHER INFORMATION: Made in Lab - Heavy chain CDR1

<400> SEQUENCE: 12

Gly Tyr Thr Phe Thr Ser Tyr Trp Met His
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Made in Lab - Heavy chain CDR2

<400> SEQUENCE: 13

Glu Ile Asn Pro Arg Asn Gly Arg Ser Asn Tyr Asn Glu Lys Phe Lys
1               5                   10                  15

Thr

<210> SEQ ID NO 14
<211> LENGTH: 14
<212> TYPE: PRT
<213> ORGANISM: Artificial Sequence
<220> FEATURE:
<223> OTHER INFORMATION: Made in Lab - Heavy chain CDR6

<400> SEQUENCE: 14

Glu Val His Tyr Tyr Gly Ser Asp Tyr Asp Ala Met Asp Tyr
1               5                   10

<210> SEQ ID NO 15
<211> LENGTH: 107
<212> TYPE: PRT
<213> ORGANISM: Artificial Sequence
<220> FEATURE:
<223> OTHER INFORMATION: Made in Lab - Varialble light chain

<400> SEQUENCE: 15

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Pro Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Phe Thr Ile Ser Asn Val Gln Ser
65                  70                  75                  80

Glu Asp Leu Ala Asp Tyr Phe Cys Gln Gln Tyr Asn Thr Tyr Pro Tyr
                85                  90                  95

Thr Phe Gly Gly Gly Thr Lys Leu Glu Ile Lys
            100                 105

<210> SEQ ID NO 16
<211> LENGTH: 123
<212> TYPE: PRT
<213> ORGANISM: Artificial Sequence
<220> FEATURE:
<223> OTHER INFORMATION: Made in Lab - Variable heavy chain

<400> SEQUENCE: 16

Glu Val Gln Leu Gln Glu Ser Gly Ala Glu Leu Val Lys Pro Gly Ala
```

```
                1               5                   10                  15
            Ser Val Lys Leu Ser Cys Lys Ala Ser Gly Tyr Thr Phe Thr Ser Tyr
                        20                  25                  30

Trp Met His Trp Val Lys Gln Arg Pro Gly Gln Gly Leu Glu Trp Ile
                        35                  40                  45

Gly Glu Ile Asn Pro Arg Asn Gly Arg Ser Asn Tyr Asn Glu Lys Phe
                        50                  55                  60

Lys Thr Lys Ala Thr Leu Thr Val Asp Arg Ser Ser Ser Thr Ala Tyr
            65                  70                  75                  80

Leu Gln Leu Ser Ser Leu Thr Ser Glu Asp Ser Ala Val Tyr Ser Cys
                        85                  90                  95

Ala Arg Glu Val His Tyr Tyr Gly Ser Asp Tyr Asp Ala Met Asp Tyr
                        100                 105                 110

Trp Gly Gln Gly Thr Ser Val Thr Val Ser Ser
                        115                 120

<210> SEQ ID NO 17
<211> LENGTH: 11
<212> TYPE: PRT
<213> ORGANISM: Artificial Sequence
<220> FEATURE:
<223> OTHER INFORMATION: Made in Lab - Light chain CDR1

<400> SEQUENCE: 17

Lys Ala Ser Gln Asp Val Asp Thr Thr Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Made in Lab - Light chain CDR2

<400> SEQUENCE: 18

Trp Ala Ser Thr Arg His Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Made in Lab - Light Chain CDR3

<400> SEQUENCE: 19

Gln Gln Tyr Thr Phe Tyr Pro Tyr Thr
1               5

<210> SEQ ID NO 20
<211> LENGTH: 10
<212> TYPE: PRT
<213> ORGANISM: Artificial Sequence
<220> FEATURE:
<223> OTHER INFORMATION: Made in Lab - Heavy chain CDR1

<400> SEQUENCE: 20

Gly Tyr Thr Phe Thr Ser Tyr Trp Met His
1               5                   10

<210> SEQ ID NO 21
<211> LENGTH: 17
<212> TYPE: PRT
```

```
<213> ORGANISM: Artificial Sequence
<220> FEATURE:
<223> OTHER INFORMATION: Made in Lab - Heavy chain CDR2

<400> SEQUENCE: 21

Glu Ile Asn Pro Arg Asn Gly Arg Ser Asn Tyr Asn Glu Lys Phe Lys
1               5                   10                  15

Thr

<210> SEQ ID NO 22
<211> LENGTH: 14
<212> TYPE: PRT
<213> ORGANISM: Artificial Sequence
<220> FEATURE:
<223> OTHER INFORMATION: Made in Lab - Heavy chain CDR6

<400> SEQUENCE: 22

Glu Val His Tyr Tyr Gly Ser Asp Tyr Asp Ala Met Asp Phe
1               5                   10

<210> SEQ ID NO 23
<211> LENGTH: 107
<212> TYPE: PRT
<213> ORGANISM: Artificial Sequence
<220> FEATURE:
<223> OTHER INFORMATION: Made in Lab - Varialble light chain

<400> SEQUENCE: 23

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asp Thr Thr
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Thr Phe Tyr Pro Tyr
                85                  90                  95

Thr Phe Gly Gly Gly Thr Lys Leu Glu Ile Lys
            100                 105

<210> SEQ ID NO 24
<211> LENGTH: 123
<212> TYPE: PRT
<213> ORGANISM: Artificial Sequence
<220> FEATURE:
<223> OTHER INFORMATION: Made in Lab - Variable heavy chain

<400> SEQUENCE: 24

Glu Val Gln Leu Gln Glu Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Arg Asn Gly Arg Ser Asn Tyr Asn Glu Lys Phe
    50                  55                  60

Lys Thr Lys Ala Thr Leu Thr Val Asp Glu Ser Ser Ser Thr Ala Tyr
65                  70                  75                  80
```

Met Gln Leu Ser Ser Leu Thr Ser Glu Asp Ser Ala Val Tyr Ser Cys
                85                  90                  95

Ala Arg Glu Val His Tyr Tyr Gly Ser Asp Tyr Asp Ala Met Asp Phe
            100                 105                 110

Trp Gly Gln Gly Thr Ser Val Thr Val Ser Pro
        115                 120

<210> SEQ ID NO 25
<211> LENGTH: 493
<212> TYPE: PRT
<213> ORGANISM: Artificial Sequence
<220> FEATURE:
<223> OTHER INFORMATION: Made in Lab - anti-BCMA CAR

<400> SEQUENCE: 25

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Pro Ser Leu
            20                  25                  30

Ala Met Ser Leu Gly Lys Arg Ala Thr Ile Ser Cys Arg Ala Ser Glu
        35                  40                  45

Ser Val Thr Ile Leu Gly Ser His Leu Ile His Trp Tyr Gln Gln Lys
    50                  55                  60

Pro Gly Gln Pro Pro Thr Leu Leu Ile Gln Leu Ala Ser Asn Val Gln
65                  70                  75                  80

Thr Gly Val Pro Ala Arg Phe Ser Gly Ser Gly Ser Arg Thr Asp Phe
                85                  90                  95

Thr Leu Thr Ile Asp Pro Val Glu Glu Asp Val Ala Val Tyr Tyr
            100                 105                 110

Cys Leu Gln Ser Arg Thr Ile Pro Arg Thr Phe Gly Gly Gly Thr Lys
        115                 120                 125

Leu Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175

Tyr Thr Phe Thr Asp Tyr Ser Ile Asn Trp Val Lys Arg Ala Pro Gly
            180                 185                 190

Lys Gly Leu Lys Trp Met Gly Trp Ile Asn Thr Glu Thr Arg Glu Pro
        195                 200                 205

Ala Tyr Ala Tyr Asp Phe Arg Gly Arg Phe Ala Phe Ser Leu Glu Thr
    210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

```
Pro Leu Ala Gly Thr Cys Gly Val Leu Leu Ser Leu Val Ile Thr
            325                 330                 335

Leu Tyr Cys Lys Arg Gly Arg Lys Leu Leu Tyr Ile Phe Lys Gln
        340                 345                 350

Pro Phe Met Arg Pro Val Gln Thr Thr Gln Glu Glu Asp Gly Cys Ser
    355                 360                 365

Cys Arg Phe Pro Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 26
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 26

Asp Gly Gly Gly Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 27

Thr Gly Glu Lys Pro
1               5

<210> SEQ ID NO 28
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 28

Gly Gly Arg Arg
1

<210> SEQ ID NO 29
<211> LENGTH: 5
<212> TYPE: PRT
<213> ORGANISM: Artificial Sequence
<220> FEATURE:
```

```
<223> OTHER INFORMATION: Exemplary linker sequence

<400> SEQUENCE: 29

Gly Gly Gly Gly Ser
1               5

<210> SEQ ID NO 30
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 30

Glu Gly Lys Ser Ser Gly Ser Gly Ser Glu Ser Lys Val Asp
1               5                   10

<210> SEQ ID NO 31
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 31

Lys Glu Ser Gly Ser Val Ser Ser Glu Gln Leu Ala Gln Phe Arg Ser
1               5                   10                  15

Leu Asp

<210> SEQ ID NO 32
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 32

Gly Gly Arg Arg Gly Gly Gly Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 33

Leu Arg Gln Arg Asp Gly Glu Arg Pro
1               5

<210> SEQ ID NO 34
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 34

Leu Arg Gln Lys Asp Gly Gly Gly Ser Glu Arg Pro
1               5                   10

<210> SEQ ID NO 35
<211> LENGTH: 16
<212> TYPE: PRT
<213> ORGANISM: Artificial Sequence
```

```
<220> FEATURE:
<223> OTHER INFORMATION: Exemplary linker sequence

<400> SEQUENCE: 35

Leu Arg Gln Lys Asp Gly Gly Ser Gly Gly Gly Ser Glu Arg Pro
1               5                   10                  15

<210> SEQ ID NO 36
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 36

Gly Ser Thr Ser Gly Ser Gly Lys Pro Gly Ser Gly Glu Gly Ser Thr
1               5                   10                  15

Lys Gly

<210> SEQ ID NO 37
<211> LENGTH: 4
<212> TYPE: PRT
<213> ORGANISM: Artificial Sequence
<220> FEATURE:
<223> OTHER INFORMATION: Exemplary rule for determining light chain
      CDR-L3 motif
<220> FEATURE:
<221> NAME/KEY: MISC_FEATURE
<222> LOCATION: (3)..(3)
<223> OTHER INFORMATION: Xaa is any amino acid

<400> SEQUENCE: 37

Phe Gly Xaa Gly
1

<210> SEQ ID NO 38
<211> LENGTH: 4
<212> TYPE: PRT
<213> ORGANISM: Artificial Sequence
<220> FEATURE:
<223> OTHER INFORMATION: Exemplary rule for determining heavy chain
      CDR-H1 motif
<220> FEATURE:
<221> NAME/KEY: MISC_FEATURE
<222> LOCATION: (2)..(4)
<223> OTHER INFORMATION: Xaa is any amino acid

<400> SEQUENCE: 38

Cys Xaa Xaa Xaa
1

<210> SEQ ID NO 39
<211> LENGTH: 5
<212> TYPE: PRT
<213> ORGANISM: Artificial Sequence
<220> FEATURE:
<223> OTHER INFORMATION: Exemplary rule for determining heavy chain
      CDR-H2 motif

<400> SEQUENCE: 39

Leu Glu Trp Ile Gly
1               5

<210> SEQ ID NO 40
<211> LENGTH: 4
<212> TYPE: PRT
<213> ORGANISM: Artificial Sequence
<220> FEATURE:
```

```
<223> OTHER INFORMATION: Exemplary rule for determining heavy chain
      CDR-H3 motif
<220> FEATURE:
<221> NAME/KEY: MISC_FEATURE
<222> LOCATION: (3)..(3)
<223> OTHER INFORMATION: Xaa is any amino acid

<400> SEQUENCE: 40

Trp Gly Xaa Gly
1

<210> SEQ ID NO 41
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is Lys or Arg
<220> FEATURE:
<221> NAME/KEY: misc_feature
<222> LOCATION: (2)..(2)
<223> OTHER INFORMATION: Xaa is Leu or Ile or Val or Phe or Thr or Ala
<220> FEATURE:
<221> NAME/KEY: misc_feature
<222> LOCATION: (3)..(3)
<223> OTHER INFORMATION: Xaa is Thr or Ser or Ile or Ala

<400> SEQUENCE: 41

Xaa Xaa Xaa
1
```

ANTI-BCMA CAR ANTIBODIES, CONJUGATES, AND METHODS OF USE

CROSS REFERENCE TO RELATED APPLICATIONS

This application is a National Stage application under 35 U.S.C. § 371 of International Application No. PCT/US2019/37274, filed Jun. 14, 2019, which claims the benefit under 35 U.S.C. § 119 (e) of U.S. Provisional Application No. 62/685,043, filed Jun. 14, 2018, which is incorporated by reference herein in its entirety.

STATEMENT REGARDING SEQUENCE LISTING

The Sequence Listing associated with this application is provided in text format in lieu of a paper copy and is hereby incorporated by reference into the specification. The .txt file contains a sequence listing entitled "TSY-09701_ST25.txt" created on Jun. 19, 2024 and is 19,079 bytes in size. The sequence listing contained in this .txt file is part of the specification and is hereby incorporated by reference herein in its entirety.

BACKGROUND

Technical Field

The present invention relates to antibody compositions. More particularly, the invention relates to antibodies and antigen binding fragments, and conjugates thereof, that bind to an anti-BCMA CAR, and methods of using the same to detect anti-BCMA CAR T cells.

Description of the Related Art

Genetic approaches offer a potential means to enhance immune recognition and elimination of cancer cells. One promising strategy is to genetically engineer immune effector cells to express a chimeric antigen receptors (CAR) that redirects cytotoxicity toward tumor cells. However, it has been difficult to precisely measure CAR expression on one or more adoptively transferred CAR T cells and the persistence of CAR T cells in vivo which confounds attempts to measure CAR T cell activity. The most common approach to assessing CAR T cells is quantitative PCR using CAR-specific primers. However, this technique is inadequate and does not allow for the multi-parameter analyses of CAR T cells.

BRIEF SUMMARY

The invention generally provides antibodies and antigen binding fragments thereof, conjugates thereof, and methods of using the same to detect, determine, or measure $CAR^+$ T cells and/or CAR expression on one or more T cells.

In various embodiments, an antibody or antigen binding fragment thereof comprises one or more CDRs that bind an anti-BCMA chimeric antigen receptor (CAR).

In particular embodiments, the one or more CDRs bind an anti-BCMA scFv domain of the anti-BCMA CAR.

In some embodiments, three light chain CDRs bind an anti-BCMA scFv domain of the anti-BCMA CAR.

In certain embodiments, three heavy chain CDRs bind an anti-BCMA scFv domain of the anti-BCMA CAR.

In particular embodiments, three light chain CDRs and three heavy chain CDRs bind an anti-BCMA scFv domain of the anti-BCMA CAR.

In certain embodiments, the antibody or antigen binding fragment thereof binds one or more epitopes of an anti-BCMA scFv sequence set forth in SEQ ID NO: 25.

In particular embodiments, the antibody or antigen binding fragment thereof is human.

In some embodiments, the antibody or antigen binding fragment thereof is humanized.

In certain embodiments, the antibody or antigen binding fragment thereof is murine.

In particular embodiments, the antibody or antigen binding fragment thereof is chimeric.

In certain embodiments, the antibody or antigen binding fragment thereof is monoclonal.

In certain embodiments, the antibody or antigen binding fragment thereof is an antigen-binding fragment.

In particular embodiments, the antibody or antigen binding fragment thereof is selected from the group consisting of: a Fab' fragments, F(ab')2 fragments, bispecific Fab dimers (Fab2), trispecific Fab trimers (Fab3), Fv, single chain Fv proteins ("scFv"), bis-scFv, (scFv)2, minibodies, diabodies, triabodies, tetrabodies, disulfide stabilized Fv proteins ("dsFv"), and single-domain antibody (sdAb, Nanobody®).

In some embodiments, the antibody or antigen binding fragment thereof is an scFv.

In various embodiments, an antibody or antigen binding fragment thereof comprises a variable light chain comprising CDRL1-CDRL3 sequences set forth in SEQ ID NOs: 1-3, and a variable heavy chain comprising CDRH1-CDRH3 sequences set forth in SEQ ID NOs: 4-6.

In further embodiments, an antibody or antigen binding fragment thereof comprises a variable light chain sequence set forth in SEQ ID NO: 7.

In particular embodiments, an antibody or antigen binding fragment thereof comprises a variable heavy chain sequence set forth in SEQ ID NO: 8.

In additional embodiments, an antibody or antigen binding fragment thereof comprises a variable light chain sequence set forth in SEQ ID NO: 7 and a variable heavy chain sequence set forth in SEQ ID NO: 8.

In various embodiments, an antibody or antigen binding fragment thereof comprises a variable light chain comprising CDRL1-CDRL3 sequences set forth in SEQ ID NOs: 9-11, and a variable heavy chain comprising CDRH1-CDRH3 sequences set forth in SEQ ID NOs: 12-14.

In certain embodiments, an antibody or antigen binding fragment thereof comprises a variable light chain sequence set forth in SEQ ID NO: 15.

In particular embodiments, an antibody or antigen binding fragment thereof comprises a variable heavy chain sequence set forth in SEQ ID NO: 16.

In some embodiments, an antibody or antigen binding fragment thereof comprises a variable light chain sequence set forth in SEQ ID NO: 15 and a variable heavy chain sequence set forth in SEQ ID NO: 16.

In various embodiments, an antibody or antigen binding fragment thereof comprises a variable light chain comprising CDRL1-CDRL3 sequences set forth in SEQ ID NOs: 17-19, and a variable heavy chain comprising CDRH1-CDRH3 sequences set forth in SEQ ID NOs: 20-22.

In particular embodiments, an antibody or antigen binding fragment thereof comprises a variable light chain sequence set forth in SEQ ID NO: 23.

In certain embodiments, an antibody or antigen binding fragment thereof comprises a variable heavy chain sequence set forth in SEQ ID NO: 24.

In some embodiments, an antibody or antigen binding fragment thereof comprises a variable light chain sequence set forth in SEQ ID NO: 23 and a variable heavy chain sequence set forth in SEQ ID NO: 24.

In particular embodiments, an antibody or antigen binding fragment thereof is human.

In certain embodiments, an antibody or antigen binding fragment thereof is humanized.

In some embodiments, an antibody or antigen binding fragment thereof is murine.

In certain embodiments, an antibody or antigen binding fragment thereof is chimeric.

In particular embodiments, an antibody or antigen binding fragment thereof is monoclonal.

In certain embodiments, an antibody or antigen binding fragment thereof is an antigen-binding fragment.

In some embodiments, an antibody or antigen binding fragment thereof is selected from the group consisting of: a Fab' fragments, F(ab')2 fragments, bispecific Fab dimers (Fab2), trispecific Fab trimers (Fab3), Fv, single chain Fv proteins ("scFv"), bis-scFv, (scFv)2, minibodies, diabodies, triabodies, tetrabodies, disulfide stabilized Fv proteins ("dsFv"), and single-domain antibody (sdAb, Nanobody®).

In certain embodiments, an antibody or antigen binding fragment thereof is an scFv.

In certain embodiments, an antibody or antigen binding fragment thereof binds one or more epitopes of an anti-BCMA scFv sequence set forth in SEQ ID NO: 25.

In various embodiments, a conjugate, comprises an antibody or antigen binding fragment thereof contemplated herein and a means for detection.

In various embodiments, a conjugate, comprises an antibody or antigen binding fragment thereof contemplated herein and a detection means.

In various embodiments, a conjugate, comprises an antibody or antigen binding fragment thereof contemplated herein and a detectable label.

In some embodiments, the detectable label is selected from the group consisting of: a hapten, a fluorescent dye, a fluorescent protein, a chromophore, a metal ion, a gold particle, a silver particle, a magnetic particle, a polypeptide, an enzyme, a luminescent compound, or an oligonucleotide.

In particular embodiments, the detectable label is a fluorescent dye selected from the group consisting of: Oregon Green®, Pacific Blue™, Pacific Orange™, Pacific Green™, Cascade Blue™, Cascade Yellow™, Lucifer Yellow™, Marina Blue™, and Texas Red® (TxRed).

In certain embodiments, the detectable label is an AlexaFluor® (AF) dye selected from the group consisting of: AF350, AF405, AF488, AF500, AF514, AF532, AF546, AF555, AF568, AF594, AF610, AF633, AF635, AF647, AF680, AF700, AF710, AF750, AF790, and AF800.

In some embodiments, the detectable label is a QDot® selected from the group consisting of: Qdot®525, Qdot®565, Qdot®585, Qdot®605, Qdot®655, Qdot®705, and Qdot®800.

In particular embodiments, the detectable label is a DyLight™ Dye (DL) selected from the group consisting of: DL549, DL649, DL680, and DL800.

In certain embodiments, the detectable label is a hapten selected from the group consisting of: fluorescein or a derivative thereof, fluorescein isothiocyanate, carboxyfluorescein, dichlorotriazinylamine fluorescein, digoxigenin, dinitrophenol (DNP), trinitrophenol (TNP), and biotin.

In particular embodiments, the detectable label is a Cy Dye selected from the group consisting of: Cy2, Cy3, Cy3.5, Cy5, Cy5.5, Cy7, and Cy 7.5.

In some embodiments, the detectable label is a fluorescent molecule selected from the group consisting of: Phycoerythrin (PE, R-Phycoerythrin (RPE)), B-Phycoerythrin (BPE), Peridinin Chlorophyll (PerCP), Allophycocyanin (APC), and C-Phycocyanin.

In particular embodiments, the detectable label is a fluorescent dye selected from the group consisting of: Atto 390, Atto 425, Atto 465, Atto 488, Atto 495, Atto 514 Atto 520, Atto 532, Atto 550, Atto 565, Atto 590, Atto 594, Atto 610, Atto 620, Atto 633, Atto 647, Atto 655, Atto 665, Atto 680, Atto 700, Atto 725, Atto 740, Super Bright™ 436, Super Bright™ 600, Super Bright™ 645, Super Bright™ 702, Super Bright™ 780, Brilliant™ Violet 421, Brilliant™ Violet 480, Brilliant™ Violet 510, Brilliant™ Violet 605, Brilliant Violet™ 650, Brilliant Violet™ 711, Brilliant Violet™ 786, Brilliant™ Ultraviolet 395 (BUV395), Brilliant™ Ultraviolet 496 (BUV496), Brilliant™ Ultraviolet 563 (BUV563), Brilliant™ Ultraviolet 661 (BUV661), Brilliant™ Ultraviolet 737 (BUV737), Brilliant™ Ultraviolet 805 (BUV805), Brilliant™ Blue 515 (BB515), Brilliant™ Blue 700 (BB700) and IR Dye 680, IR Dye 680LT, IR Dye 700, IR Dye 700DX, IR Dye 800, IR Dye 800RS, and IR Dye 800CW.

In certain embodiments, the detectable label is a tandem fluorescent dye selected from the group consisting of: RPE-Cy5, RPE-Cy5.5, RPE-Cy7, RPE-CF594, RPE-AlexaFluor® tandem conjugates; RPE-Alexa610, RPE-TxRed, APC-H7, APC-R700, APC-Alexa600, APC-Alexa610, APC-Alexa750, APC-Cy5, APC-Cy5.5, and APC-Cy7.

In certain embodiments, the detectable label is a fluorescent protein selected from the group consisting of: GFP, eGFP, BFP, CFP, YFP, DsRed, DsRed2, mRFP, mBanana, mOrange, dTomato, tdTomato, mTangerine, mStrawberry, mCherry, mPlum, and mRaspberry.

In particular embodiments, the detectable label is an enzyme selected from the group consisting of: alkaline phosphatase, horseradish peroxidase, luciferase, and β-galactosidase.

In certain embodiments, the detectable label comprises a radionuclide selected from the group consisting of: carbon (14C), chromium (51Cr), cobalt (57Co), fluorine (18F), gadolinium (153Gd, 159Gd), germanium (68Ge), holmium (166Ho), indium (115 In, 113 In, 112 In, mIn), iodine (125I, 123I, 121I), lanthanum (140La), lutetium (177Lu), manganese (54Mn), molybdenum (99 Mo), palladium (103 Pd), phosphorous (32 P), praseodymium (142 Pr), promethium (149Pm), rhenium (186Re, 188Re), rhodium (105Rh), rutheroium (97Ru), samarium (153Sm), scandium (47Sc), selenium (75Se), (85Sr), sulphur (35S), technetium (99Tc), thallium (201Ti), tin (113Sn, 117Sn), tritium (3H), xenon (133Xe), ytterbium (169Yb, 175Yb), and yttrium (90Y).

In various embodiments, a polynucleotide encodes an antibody or antigen-binding fragment thereof contemplated.

In certain embodiments, a host cell comprises an antibody or antigen-binding fragment thereof or polynucleotide contemplated herein.

In some embodiments, a composition comprises an antibody or antigen-binding fragment thereof, a conjugate, a polynucleotide, or a host cell contemplated herein.

In various embodiments, a method of producing an antibody or antigen-binding fragment thereof, comprises expressing the antibody or antigen-binding fragment thereof contemplated herein in a host cell and recovering or isolating the antibody.

In certain embodiments, a kit comprises an antibody or antigen-binding fragment thereof or conjugate contemplated herein, and instructions for use.

In particular embodiments, a method of detecting expression of an anti-BCMA CAR on a T cell, comprises contacting a T cell with the antibody or antigen-binding fragment thereof or conjugate contemplated herein and detecting the formation of an antibody:anti-BCMA CAR complex.

In various embodiments, a method of detecting expression of an anti-BCMA CAR in a population of T cells, comprises contacting a population of T cells with an antibody or antigen-binding fragment thereof or conjugate contemplated herein and detecting the formation of an antibody:anti-BCMA CAR complex on the one or more T cells.

In certain embodiments, a method of determining the expression of an anti-BCMA CAR on a T cell comprises contacting a T cell with an antibody or antigen-binding fragment thereof or a conjugate contemplated herein, detecting the formation of an antibody:anti-BCMA CAR complex, and measuring the amount of the complex to determine the expression of the anti-BCMA CAR on the T cell.

In particular embodiments, a method of determining expression of an anti-BCMA CAR in a population of T cells, comprises contacting a population of T cells with the antibody or antigen-binding fragment thereof or conjugate contemplated herein, detecting the formation of an antibody:anti-BCMA CAR complex on one or more T cells, and measuring the amount of the complex to determine the expression of the anti-BCMA CAR on the one or more T cells.

In various embodiments, a method of determining a number of anti-BCMA CAR+ T cells in a population of T cells, comprises contacting a population of T cells with an antibody or antigen-binding fragment thereof conjugate contemplated herein, detecting the formation of an antibody:anti-BCMA CAR complex on one or more T cells, and enumerating the T cells that express the anti-BCMA CAR.

In some embodiments, immunohistochemistry, enzyme-linked immunosorbent assay (ELISA), immunoadsorbent assay, chemiluminescent assay, electrochemiluminescent assay, surface plasmon resonance (SPR)-based biosensor (e.g., BIAcore™), fluorescence microscopy, or flow cytometry, fluorescence activated cell sorting (FACS) is used to detect the formation of the antibody:anti-BCMA CAR complex.

In certain embodiments, immunohistochemistry, enzyme-linked immunosorbent assay (ELISA), immunoadsorbent assay, chemiluminescent assay, electrochemiluminescent assay, surface plasmon resonance (SPR)-based biosensor (e.g., BIAcore™), fluorescence microscopy, or flow cytometry, fluorescence activated cell sorting (FACS) is used to measure the amount of the antibody:anti-BCMA CAR complex.

In particular embodiments, immunohistochemistry, enzyme-linked immunosorbent assay (ELISA), immunoadsorbent assay, chemiluminescent assay, electrochemiluminescent assay, surface plasmon resonance (SPR)-based biosensor (e.g., BIAcore™), fluorescence microscopy, or flow cytometry, fluorescence activated cell sorting (FACS) is used to enumerate the T cells that express the anti-BCMA CAR.

BRIEF DESCRIPTION OF SEVERAL VIEWS OF THE DRAWINGS

FIG. 1 shows representative FACs plots of anti-BCMA CAR antibodies binding to populations of T cells comprising an anti-BCMA CAR (SEQ ID NO: 25).

BRIEF DESCRIPTION OF THE SEQUENCE IDENTIFIERS

SEQ ID NOs: 1-3 set forth amino acid sequences of exemplary light chain CDR sequences for an antibody that binds an anti-BCMA CAR.

SEQ ID NOs: 4-6 set forth amino acid sequences of exemplary heavy chain CDR sequences for an antibody that binds an anti-BCMA CAR.

SEQ ID NO: 7 sets forth an amino acid sequence of an exemplary light chain sequences for an antibody that binds an anti-BCMA CAR.

SEQ ID NO: 8 sets forth an amino acid sequence of an exemplary heavy chain sequences for an antibody that binds an anti-BCMA CAR.

SEQ ID NOs: 9-11 set forth amino acid sequences of exemplary light chain CDR sequences for antibody that binds an anti-BCMA CAR.

SEQ ID NOs: 12-14 set forth amino acid sequences of exemplary heavy chain CDR sequences for an antibody that binds an anti-BCMA CAR.

SEQ ID NO: 15 sets forth an amino acid sequence of an exemplary light chain sequences for an antibody that binds an anti-BCMA CAR.

SEQ ID NO: 16 sets forth an amino acid sequence of an exemplary heavy chain sequences for an antibody that binds an anti-BCMA CAR.

SEQ ID NOs: 17-19 set forth amino acid sequences of exemplary light chain CDR sequences for an antibody that binds an anti-BCMA CAR.

SEQ ID NOs: 20-22 set forth amino acid sequences of exemplary heavy chain CDR sequences for an antibody that binds an anti-BCMA CAR.

SEQ ID NO: 23 sets forth an amino acid sequence of an exemplary light chain sequences for an antibody that binds an anti-BCMA CAR.

SEQ ID NO: 24 sets forth an amino acid sequence of an exemplary heavy chain sequences for an antibody that binds an anti-BCMA CAR.

SEQ ID NO: 25 sets forth an amino acid sequence of an anti-BCMA CAR bound by the antibodies comprising the sequences set forth in SEQ ID NOs: 1-24.

SEQ ID NO: 26-36 set for the amino acid sequence of various linkers.

DETAILED DESCRIPTION

A. Overview

The invention generally relates to antibodies and antigen binding fragments, and conjugates thereof, that bind an anti-BCMA chimeric antigen receptor (CAR), compositions, and methods of using the same. In particular preferred embodiments, the invention relates to antibodies, fragments, and conjugates that bind an anti-BCMA CAR set forth in SEQ ID NO: 25, compositions and uses thereof.

BCMA is a member of the tumor necrosis factor receptor superfamily (see, e.g., Thompson et al., *J. Exp. Medicine,* 192 (1): 129-135, 2000, and Mackay et al., *Annu. Rev. Immunol,* 21:231-264, 2003. BCMA binds B-cell activating factor (BAFF) and a proliferation inducing ligand (APRIL) (see, e.g., Mackay et al., 2003 and Kalled et al., *Immunological Reviews*, 204:43-54, 2005). Among nonmalignant cells, BCMA has been reported to be expressed mostly in plasma cells and subsets of mature B-cells (see, e.g., Laabi et al., *EMBO J.*, 77 (1): 3897-3904, 1992; Laabi et al., *Nucleic Acids Res.*, 22 (7): 1147-1154, 1994; Kalled et al., 2005; O'Connor et al., *J. Exp. Medicine*, 199 (1): 91-97, 2004; and Ng et al., *J. Immunol.*, 73 (2): 807-817, 2004. Mice deficient in BCMA are healthy and have normal numbers of B cells, but the survival of long-lived plasma cells is impaired (see, e.g., O'Connor et al., 2004; Xu et al., *Mol. Cell. Biol*, 21 (12): 4067-4074, 2001; and Schiemann et al., *Science*, 293 (5537): 2 111-21 14, 2001). BCMA RNA has been detected universally in multiple myeloma cells and in other lymphomas, and BCMA protein has been detected on the surface of plasma cells from multiple myeloma patients by several investigators (see, e.g., Novak et al., *Blood*, 103 (2): 689-694, 2004; Neri et al., *Clinical Cancer Research*, 73 (19): 5903-5909, 2007; Bellucci et al., *Blood*, 105 (10): 3945-3950, 2005; and Morcaux et al., *Blood*, 703 (8): 3148-3157, 2004.

Anti-BCMA CARs offer a potentially curative, one-time therapy for subjects that have multiple myeloma or B cell lymphoma. Existing methods used to correlate anti-BCMA CAR expression and activity are suboptimal and require improvement. Using existing methods, it is difficult to precisely correlate anti-BCMA CAR expression and activity both ex vivo and in vivo and to track anti-BCMA CAR T cell survival and persistence in patients. The antibodies, fragments, and conjugates contemplated herein that bind an anti-BCMA CAR, compositions and related methods of use provide a solution to these and other problems In various embodiments, an antibody or antigen binding fragment thereof that binds an anti-BCMA antibody or portion thereof is provided. In particular embodiments, an antibody or antigen binding fragment thereof may further comprise one or more detectable labels.

Methods of using the antibodies and antigen binding fragments thereof, conjugates thereof and related compositions are also disclosed herein.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below. Additional definitions are set forth throughout this disclosure.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

C. Antibodies

In particular embodiments, an antibody or antigen binding fragment thereof that binds an anti-BCMA CAR is provided.

The term "antibody" refers to a binding agent that is a polypeptide comprising at least a light chain or heavy chain immunoglobulin variable region or fragment thereof which specifically recognizes and binds one or more epitopes of an antigen, such as a peptide, lipid, polysaccharide, or nucleic acid containing an antigenic determinant, such as those recognized by an immune cell.

An "epitope" or "antigenic determinant" refers to the region of an antigen to which a binding agent binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation.

An "isolated antibody or antigen binding fragment thereof" refers to an antibody or antigen binding fragment thereof which has been identified and separated and/or recovered from a component of its natural environment.

The terms "specific binding affinity" or "specifically binds" or "specifically bound" or "specific binding" or "specifically targets" as used herein, describe binding of an antibody or antigen binding fragment thereof to an anti-BCMA CAR, at greater binding affinity than background binding. An antibody or antigen binding fragment thereof "specifically binds" to an anti-BCMA CAR if it binds to or associates with the anti-BCMA CAR with an affinity or $K_a$ (i.e., an equilibrium association constant of a particular binding interaction with units of 1/M) of, for example, greater than or equal to about $10^5$ $M^{-1}$. In certain embodiments, an antibody or antigen binding fragment thereof binds to an anti-BCMA CAR with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" antibodies or antigen binding fragments thereof have a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of an antibody or antigen binding fragment thereof contemplated herein can be readily determined using conventional techniques, e.g., by competitive ELISA (enzyme-linked immunosorbent assay), or by binding association, or displacement assays using labeled ligands, or using a surface-plasmon resonance device such as the Biacore™ T100, which is available from Biacore™, Inc., Piscataway, NJ, or optical biosensor technology such as the EPIC system or EnSpire™ that are available from Corning and Perkin Elmer respectively (see also, e.g., Scatchard et al. (1949) Ann. N.Y. Acad. Sci. 51:660; and U.S. Pat. Nos. 5,283,173; 5,468,614, or the equivalent).

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

An "antigen (Ag)" refers to a compound, composition, or substance that can stimulate the production of antibodies or a T cell response in an animal, including compositions (such as one that includes a cancer-specific protein) that are injected or absorbed into an animal. An antigen reacts with the products of specific humoral or cellular immunity, including those induced by heterologous antigens, such as the disclosed antigens. In particular embodiments, the target antigen comprises an anti-BCMA CAR.

Antibodies, include antigen binding fragments thereof, such as Camel Ig, Ig NAR, Fab fragments, Fab' fragments, F(ab')$_2$ fragments, bispecific Fab dimers (Fab2), trispecific Fab trimers (Fab3), Fv, single chain Fv proteins ("scFv"), bis-scFv, (scFv)$_2$, minibodies, diabodies, triabodies, tetrabodies, disulfide stabilized Fv proteins ("dsFv"), and single-domain antibody (sdAb, Nanobody®) and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3$_{rd}$ Ed., W. H. Freeman & Co., New York, 1997.

As would be understood by the skilled person and as described elsewhere herein, a complete antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ. Mammalian light chains are classified as λ or κ. Immunoglobulins comprising the α, δ, ε, γ, and μ heavy chains are classified as immunoglobulin (Ig)A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

Light and heavy chain variable regions contain a "framework" region interrupted by three hypervariable regions, also called "complementarity-determining regions" or "CDRs." The CDRs can be defined or identified by conventional methods, such as by sequence according to Kabat et al. (Wu, T T and Kabat, E. A., *J Exp Med.* 132 (2): 211-50, (1970); Borden, P. and Kabat E. A., *PNAS,* 84:2440-2443 (1987); (see, Kabat et al., *Sequences of Proteins of Immunological Interest*, U.S. Department of Health and Human Services, 1991, which is hereby incorporated by reference), or by structure according to Chothia et al (Chothia, C. and Lesk, A. M., *J Mol. Biol.,* 196 (4): 901-917 (1987), Chothia, C. et al, *Nature,* 342:877-883 (1989)).

Illustrative examples of rules for predicting light chain CDRs include: CDR-L1 starts at about residue 24, is preceded by a Cys, is about 10-17 residues, and is followed by a Trp (typically Trp-Tyr-Gln, but also, Trp-Leu-Gln, Trp-Phe-Gln, Trp-Tyr-Leu); CDR-L2 starts about 16 residues after the end of CDR-L1, is generally preceded by Ile-Tyr, but also, Val-Tyr, Ile-Lys, Ile-Phe, and is 7 residues; and CDR-L3 starts about 33 residues after the end of CDR-L2, is preceded by a Cys, is 7-11 residues, and is followed by Phe-Gly-XXX-Gly (SEQ ID NO: 37) (XXX is any amino acid).

Illustrative examples of rules for predicting heavy chain CDRs include: CDR-H1 starts at about residue 26, is preceded by Cys-XXX-XXX-XXX (SEQ ID NO: 38), is 10-12 residues and is followed by a Trp (typically Trp-Val, but also, Trp-Ile, Trp-Ala); CDR-H2 starts about 15 residues after the end of CDR-H1, is generally preceded by Leu-Glu-Trp-Ile-Gly (SEQ ID NO: 39), or a number of variations, is 16-19 residues, and is followed by Lys/Arg-Leu/Ile/Val/Phe/Thr/Ala-Thr/Ser/Ile/Ala (SEQ ID NO: 41); and CDR-H3 starts about 33 residues after the end of CDR-H2, is preceded by Cys-XXX-XXX (typically Cys-Ala-Arg), is 3 to 25 residues, and is followed by Trp-Gly-XXX-Gly (SEQ ID NO: 40).

In one embodiment, light chain CDRs and the heavy chain CDRs are determined according to the Kabat method In one embodiment, light chain CDRs and the heavy chain CDR2 and CDR3 are determined according to the Kabat method, and heavy chain CDR1 is determined according to the AbM method, which is a comprise between the Kabat and Clothia methods, see e.g., Whitelegg N & Rees A R, *Protein Eng.* 2000 December; 13 (12): 819-24 and *Methods Mol Biol.* 2004; 248:51-91. Programs for predicting CDRs are publicly available, e.g., AbYsis.

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to one or more epitopes of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). Illustrative examples of light chain CDRs include the CDR sequences set forth in SEQ ID NOs: 1-3, 9-11, and 17-19. Illustrative examples of heavy chain CDRs include the CDR sequences set forth in SEQ ID NOs: 4-6, 12-14, and 20-22.

References to "$V_L$" or "VL" refer to the variable region of an immunoglobulin light chain, including that of an antibody, Fv, scFv, dsFv, Fab, or other antibody fragment as disclosed herein. Illustrative examples of light chain variable regions include the light chain variable region sequences set forth in SEQ ID NOs: 7, 15, and 23.

References to "$V_H$" or "VH" refer to the variable region of an immunoglobulin heavy chain, including that of an antibody, Fv, scFv, dsFv, Fab, or other antibody fragment as disclosed herein. Illustrative examples of heavy chain variable regions include the heavy chain variable region sequences set forth in SEQ ID NOs: 8, 16, and 24.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse. In particular preferred embodiments, an antibody comprises antigen-specific binding domain that is a chimeric antibody or antigen binding fragment thereof.

In particular embodiments, the antibody is a human antibody (such as a human monoclonal antibody) or fragment thereof. Human antibodies can be constructed by combining Fv clone variable domain sequence(s) selected from human-derived phage display libraries with known human constant domain sequences(s) as described above. Alternatively, human monoclonal antibodies may be made by the hybridoma method. Human myeloma and mouse-human heteromyeloma cell lines for the production of human monoclonal antibodies have been described, for example, by Kozbor *J. Immunol.,* 133:3001 (1984); Brodeur et al., *Monoclonal Antibody Production Techniques and Applications,* pp. 51-63 (Marcel Dekker, Inc., New York, 1987); and Boerner et al., *J. Immunol.,* 147:86 (1991). In addition, transgenic animals (e.g., mice) can be used to produce a full repertoire of human antibodies in the absence of endogenous immunoglobulin production. See, e.g., Jakobovits et al., *PNAS USA,* 90:2551 (1993); Jakobovits et al., *Nature,* 362:255 (1993); Bruggermann et al., *Year in Immunol.,* 7:33 (1993). Gene shuffling can also be used to derive human antibodies from non-human, e.g., rodent antibodies, where the human antibody has similar affinities and specificities to the starting non-human antibody. (see PCT WO 93/06213 published Apr. 1, 1993). Unlike traditional humanization of non-human antibodies by CDR grafting, this technique provides completely human antibodies, which have no FR or CDR residues of non-human origin.

In one embodiment, an antibody is a "humanized" antibody. A humanized antibody is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. Humanized or other monoclonal antibodies can have additional conservative amino acid substitutions, which have substantially no effect on antigen binding or other immunoglobulin functions. Humanized antibodies can be constructed by means of genetic engineering (see for example, U.S. Pat. No. 5,585,089).

In particular embodiments, an antibody or antigen binding fragment thereof that binds an anti-BCMA CAR, includes but is not limited to a Camel Ig (a camelid antibody (VHH)), Ig NAR, Fab fragments, Fab' fragments, F(ab')$_2$ fragments, bispecific Fab dimers (Fab2), trispecific Fab trimers (Fab3), Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody®).

"Camel Ig" or "camelid VHH" as used herein refers to the smallest known antigen-binding unit of a heavy chain antibody (Koch-Nolte, et al, FASEB J., 21:3490-3498 (2007)). A "heavy chain antibody" or a "camelid antibody" refers to an antibody that contains two VH domains and no light chains (Riechmann L. et al, J. Immunol. Methods 231:25-38 (1999); WO94/04678; WO94/25591; U.S. Pat. No. 6,005,079).

"IgNAR" of "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability can be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known. Bispecific Fab dimers (Fab2) have two Fab' fragments, each binding a different antigen. Trispecific Fab trimers (Fab3) have three Fab' fragments, each binding a different antigen.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9:129-134 (2003); and Hollinger et al., PNAS USA 90:6444-6448 (1993). Triabodies and tetrabodies are also described in Hudson et al., Nat. Med. 9:129-134 (2003).

"Single domain antibody" or "sdAb" or "nanobody" refers to an antibody fragment that consists of the variable region of an antibody heavy chain (VH domain) or the variable region of an antibody light chain (VL domain) (Holt, L., et al, Trends in Biotechnology, 21 (11): 484-490).

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthün, in The Pharmacology of Monoclonal Antibodies, vol. 113, Rosenburg and Moore eds., (Springer-Verlag, New York, 1994), pp. 269-315.

In particular embodiments, the antigen binding fragment is an scFv. In particular embodiments, the scFv is a murine, human or humanized scFv. Single chain antibodies may be cloned form the V region genes of a hybridoma specific for a desired target. The production of such hybridomas has become routine. A technique which can be used for cloning the variable region heavy chain ($V_H$) and variable region light chain ($V_L$) has been described, for example, in Orlandi et al., PNAS, 1989; 86:3833-3837.

In various embodiments, an antibody or antigen binding fragment thereof that binds to an anti-BCMA CAR comprises a variable light chain sequence comprising CDRL1-CDRL3 sequences set forth in SEQ ID NOs: 1-3, 9-11, or 17-19, and/or a variable heavy chain sequence comprising CDRH1-CDRH3 sequences set forth in SEQ ID NOs: 4-6, 12-14, or 20-22.

In some embodiments, the antibody or antigen binding fragment thereof comprises a variable light chain sequence as set forth in any one of SEQ ID NOs: 7, 15, or 23 and/or a variable heavy chain sequence as set forth in any one of SEQ ID NOs: 8, 16, or 24. In some embodiments, the antibody or antigen binding fragment thereof comprises a variable light chain sequence with at least 85%, 86%, 87%, 88%, 89%, 90%, 91%, 92%, 93%, 94%, 95%, 96%, 97%, 98%, or 99% amino acid identity to the amino acid sequence set forth in any one of SEQ ID NOs: 7, 15, or 23 and/or a variable heavy chain sequence with at least 85%, 86%, 87%, 88%, 89%, 90%, 91%, 92%, 93%, 94%, 95%, 96%, 97%, 98%, or 99% amino acid identity to the amino acid sequence set forth in any one of SEQ ID NOs: 8, 16, or 24.

In one embodiment, an antibody or antigen binding fragment thereof that binds to an anti-BCMA CAR comprises light chain CDR sequences set forth in SEQ ID NOS: 1-3, 9-11, or 17-19. In a particular embodiment, an antibody or antigen binding fragment thereof that binds to an anti-BCMA antibody or antibody fragment or anti-BCMA scFv portion of an anti-BCMA CAR comprises light chain CDR sequences with at least 85%, 86%, 87%, 88%, 89%, 90%, 91%, 92%, 93%, 94%, 95%, 96%, 97%, 98%, or 99% amino acid identity to the light chain CDR sequences set forth in SEQ ID NOs: 1-3, 9-11, or 17-19.

In one embodiment, an antibody or antigen binding fragment thereof that binds to an anti-BCMA CAR comprises heavy chain CDR sequences set forth in SEQ ID NOs: 4-6, 12-14, or 20-22. In a particular embodiment, an antibody or antigen binding fragment thereof that binds to an anti-BCMA CAR comprises heavy chain CDR sequences with at least 85%, 86%, 87%, 88%, 89%, 90%, 91%, 92%, 93%, 94%, 95%, 96%, 97%, 98%, or 99% amino acid identity to the heavy chain CDR sequences set forth in SEQ ID NOs: 4-6, 12-14, or 20-22.

In particular embodiments, an antibody or antigen binding fragment thereof that binds to an anti-BCMA CAR comprises one or more light chain CDRs as set forth in any one of SEQ ID NOs: 1-3 and/or one or more heavy chain CDRs as set forth in any one of SEQ ID NOs: 4-6. In certain embodiments, the antibody or antigen binding fragment thereof comprises a variable light chain sequence as set forth in SEQ ID NO: 7 and/or a variable heavy chain sequence as set forth in SEQ ID NO: 8.

In some embodiments, an antibody or antigen binding fragment thereof that binds to an anti-BCMA CAR comprises one or more light chain CDRs as set forth in any one of SEQ ID NOs: 9-11 and/or one or more heavy chain CDRs as set forth in any one of SEQ ID NOs: 12-14. In further embodiments, the antibody or antigen binding fragment thereof comprises a variable light chain sequence as set forth in SEQ ID NO: 15 and/or a variable heavy chain sequence as set forth in SEQ ID NO: 16.

In additional embodiments, an antibody or antigen binding fragment thereof that binds to an anti-BCMA CAR comprises one or more light chain CDRs as set forth in any one of SEQ ID NOs: 17-19 and/or one or more heavy chain CDRs as set forth in any one of SEQ ID NOs: 20-22. In particular embodiments, the antibody or antigen binding fragment thereof comprises a variable light chain sequence as set forth in SEQ ID NO: 23 and/or a variable heavy chain sequence as set forth in SEQ ID NO: 24.

In some embodiments, the antibody or antigen binding fragment thereof comprises a variable light chain sequence and/or a variable heavy chain sequence that bind an anti-BCMA CAR set forth in SEQ ID NO: 25.

D. Conjugates

In various embodiments, a conjugate comprising an antibody or antigen binding fragment thereof and a label is provided. In preferred embodiments, a conjugate comprises an antibody or antigen binding fragment thereof that binds an anti-BCMA CAR, and a detectable label or a label capable of producing a detectable signal. In more preferred embodiments, a conjugate comprises an antibody or antigen binding fragment thereof that binds an anti-BCMA CAR, coupled to a detectable label. In even more preferred embodiments, a conjugate comprises an antibody or antigen binding fragment thereof that binds an anti-BCMA CAR, covalently bound, or chemically coupled to, a detectable label.

As used herein, the term "label" refers to a detectable label or a label capable of producing a detectable signal. In particular embodiments, a label comprises a radionuclides, nucleic acid, small molecule, or polypeptide. In some embodiments, labels are directly detectable. In some embodiments, labels are indirectly detectable.

Illustrative examples of detectable labels suitable for use in conjugates contemplated in particular embodiments include, but are not limited to: haptens, fluorescent molecules, fluorescent dyes, fluorescent proteins, chromophores, metal ions, gold particles, silver particles, magnetic particles, radionuclides, polypeptides, enzymes, luminescent compounds, or oligonucleotides.

Illustrative examples of molecules suitable for use as detectable labels in particular embodiments include, but are not limited to: Oregon Green®; Pacific Blue™; Pacific Orange™; Pacific Green™; Cascade Blue™; Cascade Yellow™; Lucifer Yellow™; Marina Blue™; Texas Red® (TxRed); AlexaFluor® (AF) dyes, e.g., AF350, AF405, AF488, AF500, AF514, AF532, AF546, AF555, AF568, AF594, AF610, AF633, AF635, AF647, AF680, AF700, AF710, AF750, AF790, and AF800; QDot® nanocrystals, e.g., Qdot®525, Qdot®565, Qdot®585, Qdot®605, Qdot®655, Qdot®705, and Qdot®800; DyLight™ Dyes (DL), e.g., DL549, DL649, DL680, and DL800; fluorescein or a derivative thereof, e.g., fluorescein isothiocyanate, carboxyfluorescein, and dichlorotriazinylamine fluorescein; digoxigenin; dinitrophenol (DNP); trinitrophenol (TNP); biotin; Cy dyes, e.g., Cy2, Cy3, Cy3.5, Cy5, Cy5.5, Cy7, and Cy 7.5; Phycocrythrin (PE, R-Phycocrythrin (RPE)); B-Phycocrythrin (BPE); Peridinin Chlorophyll (PerCP); Allophycocyanin (APC); C-Phycocyanin; Atto® Dyes, e.g., Atto 390, Atto 425, Atto 465, Atto 488, Atto 495, Atto 514 Atto 520, Atto 532, Atto 550, Atto 565, Atto 590, Atto 594, Atto 610, Atto 620, Atto 633, Atto 647, Atto 655, Atto 665, Atto 680, Atto 700, Atto 725, and Atto 740; Super Bright™ Dyes, e.g., Super Bright™ 436, Super Bright™ 600, Super Bright™ 645, Super Bright™ 702, and Super Bright™ 780; Brilliant™ Dyes, e.g., Brilliant™ Violet 421, Brilliant™ Violet 480, Brilliant™ Violet 510, Brilliant™ Violet 605, Brilliant Violet™ 650, Brilliant Violet™ 711, Brilliant Violet™ 786, Brilliant™ Ultraviolet 395 (BUV395), Brilliant™ Ultraviolet 496 (BUV496), Brilliant™ Ultraviolet 563 (BUV563), Brilliant™ Ultraviolet 661 (BUV661), Brilliant™ Ultraviolet 737 (BUV737), Brilliant™ Ultraviolet 805 (BUV805), Brilliant™ Blue 515 (BB515), and Brilliant™ Blue 700 (BB700); and IR Dyes, e.g., IR Dye 680, IR Dye 680LT, IR Dye 700, IR Dye 700DX, IR Dye 800, IR Dye 800RS, and IR Dye 800CW.

Illustrative examples of tandem fluorescent dye molecules suitable for use as detectable labels include, but are not limited to: RPE-Cy5, RPE-Cy5.5, RPE-Cy7, RPE-CF594, RPE-AlexaFluor® tandem conjugates; RPE-Alexa610, RPE-TxRed, APC-H7, APC-R700, APC-Alexa600, APC-Alexa610, APC-Alexa750, APC-Cy5, APC-Cy5.5, and APC-Cy7.

Illustrative examples of fluorescent proteins suitable for use as detectable labels include, but are not limited to: GFP, cGFP, BFP, CFP, YFP, DsRed, DsRed2, mRFP, mBanana, mOrange, dTomato, tdTomato, mTangerine, mStrawberry, mCherry, mPlum, and mRaspberry.

Illustrative examples of enzymes suitable for use as detectable labels include, but are not limited to: alkaline phosphatase, horseradish peroxidase, luciferase, and β-galactosidase.

Illustrative examples of radionuclides suitable for use as detectable labels include, but are not limited to: carbon (14C), chromium (51Cr), cobalt (57Co), fluorine (18F), gadolinium (153Gd, 159Gd), germanium (68Ge), holmium (166Ho), indium (115 In, 113 In, 112 In, mIn), iodine (125I, 123I, 121I), lanthanium (140La), lutetium (177Lu), manganese (54Mn), molybdenum (99 Mo), palladium (103 Pd), phosphorous (32 P), prascodymium (142 Pr), promethium (149Pm), rhenium (186Re, 188Re), rhodium (105Rh), rutheroium (97Ru), samarium (153Sm), scandium (47Sc), selenium (75Sc), (85Sr), sulphur (35S), technetium (99Tc), thallium (201Ti), tin (113Sn, 117Sn), tritium (3H), xenon (133Xe), ytterbium (169Yb, 175Yb), and yttrium (90Y).

In particular embodiments, a conjugate comprises an antibody or antibody fragment that is conjugated, coupled, or linked (e.g., covalently bonded) to one or more labels. In certain embodiments, a label may be conjugated, coupled, or linked to an antibody or fragment either directly or indirectly (e.g., via a linker group). An antibody can be directly covalently bound to one or more labels when the antibody and the label each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

In particular embodiments, it may be desirable to couple, conjugate, or link an antibody or antibody fragment to one or more labels via a monovalent or polyvalent linker or a spacer. A linker or spacer can be used to provide sufficient distance between an antibody and a label to avoid steric hindrance or interference with antibody binding capabilities. It will be evident to those skilled in the art that a variety of bifunctional or polyfunctional reagents, both homo- and hetero-functional (such as those described in the catalog of the Pierce Chemical Co., Rockford, IL), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

In certain embodiments, a linker has an overall chain length of about 1-100 atoms, 1-80 atoms, 1-60 atoms, 1-40 atoms, 1-30 atoms, 1-20 atoms, or 1, 2, 3, 4, 5, 6, 7, 8, 9, 10, 11, 12, 13, 14, 15, 16, 17, 18, 19, or 20 atoms, wherein the atoms in the chain comprise C, S, N, P, and O.

Illustrative examples of linkers or linkages useful in particular embodiments of the present invention include, but are not limited to one or more of the following: —C(O)—, —NH—C(O)—, —C(O)—NH—, —C(O)—NH—$(CH_2)_{2-6}$—NH—C(O)—, —NH—$(CH_2)_{2-6}$—NH—C(O)—, -triazole-$(CH_2)_{2-6}$—NH—C(O)—, —S$(CH_2)_{2-6}$—NH—C(O)—, —S—$(CH_2)_{0-6}$—CH(CONH$_2$)—$(CH_2)_{0-6}$—NH—C(O)—, —S—$(CH_2)_{0-6}$—CH(CONH-PEG)-$(CH_2)_{0-6}$—NH—C(O)—, —S—S—$(CH_2)_{2-6}$—NH—C(O)—, —S—S—$(CH_2)_{0-6}$—CH(CONH$_2$)—$(CH_2)_{0-6}$—NH—C(O)—, —S—S—$(CH_2)_{0-6}$—CH(CONH-PEG)-$(CH_2)_{0-6}$—NH—C(O)—, —NH—$(CH_2)_{0-6}$—CH(CONH-PEG)-$(CH_2)_{0-6}$—NH—C(O)—, —NH—$(CH_2)_{0-6}$—CH(CONH$_2$)—$(CH_2)_{0-6}$—NH—C(O)— —C=N—O—$(CH_2)_{2-6}$—NH—C(O)—, —C=N—NH—(CO)—$(CH_2)_{2-6}$—NH—C(O)—, -succinimide-$(CH_2)_{2-6}$—NH—C(O)—, -diazodicarboxamide-(Phenyl)-J-$(CH_2)_{2-6}$—NH—C(O)—, J is O, CH$_2$, NH, S, NH (CO), (CO)NH, —NH—$(CH_2)_{2-6}$—, $(CH_2)_{1-6}$—NH—C(O)—NH—$(CH_2)_{2-6}$—, —C(S)—$(CH_2)_{0-6}$—, —$(CH_2)_{1-6}$—C(O)—NH—$(CH_2)_{2-6}$—, —$(CH_2)_{1-6}$—NH—C(O)—$(CH_2)_{2-6}$—, —$(CH_2)_{1-6}$—O—C(O)—NH—$(CH_2)_{2-6}$—, —$(CH_2)_{1-6}$—NH—C(O)—O—$(CH_2)_{2-6}$—, $(CH_2)_{1-6}$—NH—$(CH_2)_{2-6}$, $(CH_2)_{1-6}$—C(O—$(CH_2)_{2-6}$—, branched or unbranched-C1-C16-alkyl, branched or unbranched-C1-C16-alkyl where one of the carbon atoms can be optionally substituted with a heteroatom, R$^2$—NH—$(CH_2)_{2-6}$—NH—C(O)—, R$^2$—S—$(CH_2)_{2-6}$—NH—C(O)—, R$^2$-triazole-$(CH_2)_{2-6}$—NH—C(O)—, R$^2$—NH—O—$(CH_2)_{2-6}$—NH—C(O), R$^2$=N—NH—(CO)—$(CH_2)_{2-6}$—NH—C(O)—, R$^2$ is one to three bifunctional or trifunctional substituted cross-linking organic radicals selected from the group consisting of alkyl, substituted alkyl, cycloalkyl, aryl, heteroaryl, polyethylene glycol (PEG) [i.e., —(CH$_2$CH$_2$O)$_{1-20}$].

In particular embodiments, a conjugate comprises an antibody or antibody fragment covalently bound to a polypeptide-based label, e.g., a fluorescent protein or enzyme, via a polypeptide linker contemplated elsewhere herein, infra.

In preferred embodiments, a conjugate comprises an antibody or antigen binding fragment thereof that binds to an anti-BCMA CAR, covalently bound to a PE label.

E. Polypeptides

Various polypeptides, fusion polypeptides, and polypeptide variants are contemplated herein, including, but not limited to antibodies and antigen binding fragments thereof. In preferred embodiments, a polypeptide comprises an antibody or antigen binding fragment thereof that binds an anti-BCMA CAR.

"Polypeptide," "peptide" and "protein" are used interchangeably, unless specified to the contrary, and according to conventional meaning, i.e., as a sequence of amino acids. Polypeptides are not limited to a specific length, e.g., they may comprise a full-length polypeptide or a polypeptide fragment, and may include one or more post-translational modifications of the polypeptide, for example, glycosylations, acetylations, phosphorylations and the like, as well as other modifications known in the art, both naturally occurring and non-naturally occurring.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of an antibody or antigen binding fragment thereof by introducing one or more amino acid substitutions, deletions, additions and/or insertions. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence.

Polypeptides include "polypeptide fragments." Polypeptide fragments refer to a polypeptide, which can be monomeric or multimeric that has an amino-terminal deletion, a carboxyl-terminal deletion, and/or an internal deletion or substitution of a naturally-occurring or recombinantly-produced polypeptide. Illustrative examples of biologically active polypeptide fragments include antibody fragments. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In preferred embodiments, the biological activity is binding affinity to an epitope. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an antibody, useful fragments include, but are not limited to: one or more CDR regions, a CDR3 region of the heavy or light chain; a variable region of a heavy or light chain; a portion of an antibody chain or variable region including two CDRs; and the like.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82:488-492), Kunkel et al., (1987, *Methods in Enzymol,* 154:367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (Natl. Biomed. Res. Found., Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

Polypeptide variants further include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

In particular embodiments, polypeptides comprise a polypeptide linker. A "linker" refers to a plurality of amino acid residues between two or more polypeptide domains added for appropriate spacing, conformation, and function of the molecule.

In particular embodiments, the polypeptide linker is a variable region linking sequence. A "variable region linking sequence," is an amino acid sequence that connects the $V_H$ and $V_L$ domains and provides a spacer function compatible with interaction of the two sub-binding domains so that the resulting polypeptide retains a specific binding affinity to the same target molecule as an antibody that comprises the same light and heavy chain variable regions.

In particular embodiments, a conjugate comprises a polypeptide linker that covalently binds an antibody or antibody fragment to one or more protein-based labels, e.g., fluorescent protein or enzyme.

Illustrated examples of linkers suitable for use in particular embodiments contemplated herein include, but are not limited to the following amino acid sequences: GGG; DGGGS (SEQ ID NO: 26); TGEKP (SEQ ID NO: 27) (see, e.g., Liu et al., PNAS 5525-5530 (1997)); GGRR (SEQ ID NO: 28) (Pomerantz et al. 1995, supra); (GGGGS), wherein n=1, 2, 3, 4 or 5 (SEQ ID NO: 29) (Kim et al., PNAS 93, 1156-1160 (1996.); EGKSSGSGSESKVD (SEQ ID NO: 30) (Chaudhary et al., 1990, Proc. Natl. Acad. Sci. U.S.A. 87:1066-1070); KESGSVSSEQLAQFRSLD (SEQ ID NO: 31) (Bird et al., 1988, Science 242:423-426), GGRRGGGS (SEQ ID NO: 32); LRQRDGERP (SEQ ID NO: 33); LRQKDGGGSERP (SEQ ID NO: 34); LRQKD (GGGS): ERP (SEQ ID NO: 35). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods.

In one embodiment, the linker comprises the following amino acid sequence: GSTSGSGKPGSGEGSTKG (SEQ ID NO: 36) (Cooper et al., *Blood,* 101 (4): 1637-1644 (2003)).

In preferred embodiments, a polypeptide comprises the amino acid sequence set forth in SEQ ID NOs: 1-24.

F. Polynucleotides

In preferred embodiments, a polynucleotide encoding an antibody or antigen binding fragment thereof that binds an anti-BCMA CAR is provided. As used herein, the terms "polynucleotide" or "nucleic acid" refers to messenger RNA (mRNA), RNA, genomic DNA (gDNA), complementary DNA (cDNA) or recombinant DNA.

Polynucleotides include single and double stranded polynucleotides. In particular embodiments, polynucleotides include polynucleotides or variants having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences contemplated herein. In various illustrative embodiments, polynucleotides encoding a polypeptide contemplated herein, including, but not limited to the polypeptide sequences set forth in SEQ ID NOs: 1-24.

In particular embodiments, polynucleotides are provided that encode at least about 5, 10, 25, 50, 100, 150, 200, 250, 300, 350, 400, 500, 1000, 1250, 1500, 1750, or 2000 or more contiguous amino acid residues of a polypeptide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

Polynucleotide variants include polynucleotide fragments that encode biologically active polypeptide fragments or variants. As used herein, the term "polynucleotide fragment" refers to a polynucleotide fragment at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more nucleotides in length that encodes a polypeptide variant that retains at least 100%, at least 90%, at least 80%, at least 70%, at least 60%, at least 50%, at least 40%, at least 30%, at least 20%, at least 10%, or at least 5% of the naturally occurring polypeptide activity. Polynucleotide fragments refer to a polynucleotide that encodes a polypeptide that has an amino-terminal deletion, a carboxyl-terminal deletion, and/or an internal deletion or substitution of one or more amino acids of a naturally-occurring or recombinantly-produced polypeptide.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., Current Protocols in Molecular Biology, John Wiley & Sons Inc, 1994-1998, Chapter 15.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native sequence. Nonetheless, polynucleotides that vary due to differences in codon usage are specifically contemplated in particular embodiments, for example polynucleotides that are optimized for human and/or primate codon selection.

Polynucleotides can be prepared, manipulated and/or expressed using any of a variety of well-established techniques known and available in the art. In order to express a desired polypeptide, a nucleotide sequence encoding the polypeptide, can be inserted into appropriate vector.

G. Compositions

The compositions contemplated herein may comprise one or more antibodies or antibody fragments and antigen binding fragments thereof, conjugates, polypeptides, and polynucleotides. Compositions include, but are not limited to pharmaceutical compositions. There is virtually no limit to other components that may also be included in the compositions, provided that the additional agents do not adversely affect the function or activity of the active ingredient of the composition.

In particular embodiments, compositions of the present invention comprise an amount of an antibody or antigen binding fragment thereof or conjugate. As used herein, the term "amount" refers to "an amount effective" or "an effective amount" of an antibody to bind a target polypeptide.

Compositions may further comprise one or more carriers or excipients.

Illustrative examples of carriers suitable for incorporation into the compositions contemplated herein include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Acceptable carriers also include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

H. Kits

In various embodiments, a kit comprising one or more antibodies or antigen-binding fragments thereof that bind an anti-BCMA CAR and instructions for using the antibodies to detect, determine, and/or measure anti-BCMA CAR expression on one or more immune effector cells or anti-BCMA CAR T cells is provided.

In particular embodiments, a kit comprising one or more antibodies or antigen-binding fragments thereof that bind an anti-BCMA CAR and instructions for using the antibodies to detect, determine, measure and/or enumerate anti-BCMA CAR expression on one or more immune effector cells or anti-BCMA CAR T cells is provided.

In various embodiments, an antibody or antigen binding fragment thereof that binds to an anti-BCMA CAR comprises a variable light chain sequence comprising CDRL1-CDRL3 sequences set forth in SEQ ID NOs: 1-3, 9-11, or 17-19, and/or a variable heavy chain sequence comprising CDRH1-CDRH3 sequences set forth in SEQ ID NOs: 4-6, 12-14, or 20-22.

In some embodiments, the antibody or antigen binding fragment thereof comprises a variable light chain sequence as set forth in any one of SEQ ID NOs: 7, 15, or 23 and/or a variable heavy chain sequence as set forth in any one of SEQ ID NOs: 8, 16, or 24.

In some embodiments, the antibody or antigen binding fragment thereof comprises a variable light chain sequence and/or a variable heavy chain sequence that bind an anti-BCMA scFv fragment set forth in SEQ ID NO: 25.

In particular embodiments, kits comprise an antibody or antibody fragment and a detectable label and instructions for conjugation. In particular embodiments, kits comprise an antibody or antibody fragment conjugated to a detectable label and instructions for use. In preferred embodiments, the detectable label is directly detectable. In a more preferred embodiment, the detectable label is a fluorescent label. In an even more preferred embodiment, the detectable label is RPE.

I. Methods

Anti-BCMA CAR T cell activity is related, in part, to anti-BCMA CAR expression on immune effector cells. The ability to accurately assess anti-BCMA CAR expression both ex vivo or in vitro and in vivo is needed to estimate drug product activity and to track anti-BCMA CAR T cell survival and persistence in patients.

In particular embodiments, methods of using one or more antibodies or antigen binding fragments thereof are provided. The antibodies are used to detect or measure the expression of an anti-BCMA CAR. The antibodies, fragments, and conjugates contemplated herein are used to bind, detect, determine, identify, measure, quantify, and/or enumerate the presence or level of anti-BCMA CAR expression and/or numbers of anti-BCMA CAR$^+$ immune effector cells in a population.

In various embodiments, a method comprises detecting anti-BCMA CAR expression on an immune effector cell. An immune effector cell, e.g., T cell, NK cell, NKT cell, is contacted with an antibody or antigen-binding fragment thereof that binds one or more epitopes of an anti-BCMA CAR in an amount effective and for a time sufficient for the antibody to bind the anti-BCMA CAR and form an antibody:anti-BCMA CAR complex.

In particular embodiments, a method comprises detecting anti-BCMA CAR expression on one or more immune effector cells in a population of immune effector cells. One or more immune effector cells, e.g., T cells, NK cells, NKT cells, are contacted with an antibody or antigen-binding fragment thereof that binds one or more epitopes of an anti-BCMA CAR in an amount effective and for a time sufficient for the antibody to bind the anti-BCMA CAR and form an antibody:anti-BCMA CAR complex. In a particular embodiment, at least 25% of the immune effector cells are anti-BCMA CAR$^+$. In another embodiment, at least at least 50% of the immune effector cells are anti-BCMA CAR$^+$. In another embodiment, at least at least 75% of the immune effector cells are anti-BCMA CAR$^+$.

In certain embodiments, a method comprises determining the amount of expression of an anti-BCMA CAR on an immune effector cell. An immune effector cell, e.g., T cell, NK cell, NKT cell, is contacted with an antibody or antigen-binding fragment thereof that binds one or more epitopes of an anti-BCMA CAR in an amount effective and for a time sufficient for the antibody to bind the anti-BCMA CAR and form an antibody:anti-BCMA CAR complex. The amount of the antibody:anti-BCMA CAR complex is measured and compared to a control.

In some embodiments, a method comprises determining the amount of expression of an anti-BCMA CAR on one or more immune effector cells in a population of immune effector cells. One or more immune effector cells, e.g., T cells, NK cells, NKT cells, are contacted with an antibody or antigen-binding fragment thereof that binds one or more epitopes of an anti-BCMA CAR in an amount effective and for a time sufficient for the antibody to bind the anti-BCMA CAR and form an antibody:anti-BCMA CAR complex. The amount of the antibody:anti-BCMA CAR complex is measured and compared to a control.

In particular embodiments, a method comprises determining a number of anti-BCMA CAR$^+$ immune effector cells in a population of immune effector cells. One or more immune effector cells, e.g., T cells, NK cells, NKT cells, are contacted with an antibody or antigen-binding fragment thereof that binds one or more epitopes of an anti-BCMA scFv portion of a CAR in an amount effective and for a time sufficient for the antibody to bind the anti-BCMA CAR and form an antibody:anti-BCMA CAR complex. Immune effector cells comprising an antibody:anti-BCMA CAR complex can then be enumerated.

In particular embodiments, methods of detecting, determining, or enumerating anti-BCMA CAR expression or anti-BCMA CAR$^+$ T cells comprise isolation of a biological sample from a subject administered anti-BCMA CAR$^+$ T cells. In particular embodiments, the sample contains or is suspected of containing anti-BCMA CAR$^+$ T cells. In preferred embodiments, the sample is an apheresis sample, a leukapheresis sample, peripheral blood, bone marrow, lymph node tissue, cord blood, thymus tissue, tissue from a site of infection, ascites, pleural effusion, spleen tissue, or tumor biopsy. In particular embodiments, the antibodies and conjugates contemplated herein that bind an anti-BCMA CAR are used to study the pharmacokinetics, expansion, and/or persistence are measured or assessed by detecting the amount of anti-BCMA CAR$^+$ T cells in a subject and/or in samples collected from the subject at one or more time points. In particular embodiments, samples are collected, isolated, and/or harvested from a subject about 24 hours, about 48 hours, about 72 hours, about 4 days, about 5 days, about 6 days, about 7 days, about 10 days, about 14 days, about 21 days, about 3 weeks, about 4 weeks, about 5 weeks, about 6 weeks, about 7 weeks, about 8 weeks, about 9 weeks, about 10 weeks, about 11 weeks, about 12 weeks, about 3 months, about 4 months, about 6 months, about one year, or weekly, monthly, or yearly after the subject was administered the anti-BCMA CAR$^+$ T cells.

In various embodiments, an antibody or antigen binding fragment thereof that binds to an anti-BCMA CAR comprises a variable light chain sequence comprising CDRL1-CDRL3 sequences set forth in SEQ ID NOs: 1-3, 9-11, or 17-19, and/or a variable heavy chain sequence comprising CDRH1-CDRH3 sequences set forth in SEQ ID NOs: 4-6, 12-14, or 20-22.

In some embodiments, an antibody or antigen binding fragment thereof comprises a variable light chain sequence as set forth in any one of SEQ ID NOs: 7, 15, or 23 and/or a variable heavy chain sequence as set forth in any one of SEQ ID NOs: 8, 16, or 24.

In some embodiments, an antibody or antigen binding fragment thereof comprises a variable light chain sequence and/or a variable heavy chain sequence that bind an anti-BCMA CAR set forth in SEQ ID NO: 25.

In particular embodiments, methods of detecting, determining, or enumerating anti-BCMA CAR expression or anti-BCMA CAR$^+$ T cells comprise use of an antibody or antibody fragment conjugated to a detectable label. In preferred embodiments, the detectable label is directly detectable. In a more preferred embodiment, the detectable label is a fluorescent label. In an even more preferred embodiment, the detectable label is RPE.

The presence of the antibody:anti-BCMA CAR complex can be detected, determined, and/or enumerated in particular embodiments, using one or more of the following assays:

immunohistochemistry, enzyme-linked immunosorbent assay (ELISA), immunoadsorbent assay, chemiluminescent assay, electrochemiluminescent assay, surface plasmon resonance (SPR)-based biosensor (e.g., BIAcore™), fluorescence microscopy, flow cytometry, fluorescence activated cell sorting (FACS) or Western blot.

In preferred embodiments, the presence of the antibody:anti-BCMA CAR complex is detected, determined, and/or enumerated using flow cytometry. In a more preferred embodiment, the presence of the antibody:anti-BCMA CAR complex is detected, determined, and/or enumerated using FACs.

In particular embodiments, a level of background expression of the anti-BCMA CAR on one or more immune effector cells is determined and subtracted from the amount of antibody:anti-BCMA CAR complex measured on one or more immune effector cells or used to normalize the measurements.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Evaluation of Antibodies Directed Against an Anti-BCMA CAR

Mouse monoclonal antibodies were generated against the anti-BCMA CAR sequence set forth in SEQ ID NO: 25.

Peripheral blood mononuclear cells (PBMC) were cultured in static flasks in media containing IL-2 (CellGenix) and antibodies specific for CD3 and CD28 (Miltenyi Biotec). $2 \times 10^8$ transducing units of lentivirus encoding anti-BCMA CARs were added one day after culture initiation. Anti-BCMA CAR T cells were maintained in log-phase by adding fresh media containing IL-2 for a total of ten days of culture. T cells transduced with an anti-BCMA CAR (BCMA-02), a humanized anti-BCMA CAR (BCMA-03), or an anti-EGFR CAR and expanded for 10 days. CAR T cells were assessed for CAR expression at the end of culture using three antibodies directed against the anti-BCMA scFv sequence set forth in SEQ ID NO: 25.

Antibody clones 7G2.A1.B2, 11E6.G2.B5, and 11E6.G7.F2 were conjugated to phycoerythrin (PE). $1 \times 10^6$ anti-BCMA CAR T cells or untransduced control T cells were incubated 100 μL total volume with 1 μg of the antibody conjugate for 20 minutes at 4° C. and then washed and fixed in 1% paraformaldehyde. FACS analyses was performed on the samples to detect, determine, and enumerate anti-BCMA CAR+ T cells. All antibody conjugates detected anti-BCMA CAR expression on about 70% of the cells. FIG. 1.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An antibody or antigen binding fragment thereof that binds an anti-BCMA scFv domain of an anti-BCMA CAR comprising a variable light chain comprising CDRL1-CDRL3 sequences set forth in SEQ ID NOs: 1-3 or 9-11; and a variable heavy chain comprising CDRH1-CDRH3 sequences set forth in SEQ ID NOs: 4-6 or 12-14.

2. The antibody or antigen binding fragment thereof of claim 1, wherein the antibody or antigen binding fragment thereof binds one or more epitopes of an anti-BCMA scFv sequence set forth in SEQ ID NO: 25.

3. The antibody or antigen binding fragment thereof of claim 1, comprising a variable light chain sequence having 90% amino acid identity to an amino acid sequence as set forth in SEQ ID NO: 7 or 15.

4. The antibody or antigen binding fragment thereof of claim 1, comprising a variable heavy chain sequence having 90% amino acid identity to an amino acid sequence as set forth in SEQ ID NO: 8, 16, or 24.

5. The antibody or antigen binding fragment thereof of claim 1, comprising a variable light chain sequence having 90% amino acid identity to an amino acid sequence as set forth in SEQ ID NO: 7 or 15; and a variable heavy chain sequence having 90% amino acid identity to an amino acid sequence as set forth in SEQ ID NO: 8, 16, or 24.

6. The antibody or antigen binding fragment thereof of claim 1, wherein the antibody or antigen binding fragment thereof is murine, human, humanized, or chimeric.

7. The antibody or antigen binding fragment thereof of claim 1, wherein the antibody or antigen binding fragment thereof is monoclonal.

8. The antibody or antigen binding fragment thereof of claim 1, wherein the antibody or antigen binding fragment thereof is selected from the group consisting of: a Fab' fragments, F(ab')$_2$ fragments, bispecific Fab dimers (Fab2), trispecific Fab trimers (Fab3), Fv, single chain Fv proteins ("scFv"), bis-scFv, (scFv)$_2$, minibodies, diabodies, triabodies, tetrabodies, disulfide stabilized Fv proteins ("dsFv"), and single-domain antibody (sdAb).

9. A conjugate, comprising the antibody or antigen binding fragment thereof of claim 1 and a detectable label.

10. The conjugate of claim 9, wherein the detectable label is selected from the group consisting of: a hapten, a fluorescent dye, a fluorescent protein, a chromophore, a metal ion, a gold particle, a silver particle, a magnetic particle, a polypeptide, an enzyme, a luminescent compound, or an oligonucleotide.

11. The conjugate of claim 9, wherein the detectable label is a dye selected from the group consisting of: AF350, AF405, AF488, AF500, AF514, AF532, AF546, AF555, AF568, AF594, AF610, AF633, AF635, AF647, AF680, AF700, AF710, AF750, AF790, and AF800.

12. The conjugate of claim 11, wherein the detectable label is AF488.

13. A composition comprising the antibody or antigen-binding fragment thereof of claim 1.

14. A kit comprising the antibody or antigen-binding fragment thereof of claim 1, and instructions for use.

* * * * *

UNITED STATES PATENT AND TRADEMARK OFFICE
CERTIFICATE OF CORRECTION

Page 1 of 1

PATENT NO. : 12,247,084 B2
APPLICATION NO. : 16/973877
DATED : March 11, 2025
INVENTOR(S) : Kevin Friedman et al.

It is certified that error appears in the above-identified patent and that said Letters Patent is hereby corrected as shown below:

In the Claims

Column 48, Claim 13, Lines 58-59: Please replace "antigen-binding" with "antigen binding".

Column 48, Claim 14, Line 60: Please replace "antigen-binding" with "antigen binding".

Signed and Sealed this
Second Day of September, 2025

Coke Morgan Stewart
*Acting Director of the United States Patent and Trademark Office*